US006258230B1

United States Patent
Shen et al.

(10) Patent No.: US 6,258,230 B1
(45) Date of Patent: Jul. 10, 2001

(54) NON-ENZYMATIC DISPOSABLE URIC ACID DETECTING ELECTRODE STRIP, METHOD FOR PRODUCING THE SAME AND ITS USE

(75) Inventors: Yen-Shih Shen; Chun-Lung Hsieh; Kun-Lieh Wu, all of Hsinchu (TW)

(73) Assignee: Apex Biotechnology COrporation (TW)

( * ) Notice: Subject to any disclaimer, the term of this patent is extended or adjusted under 35 U.S.C. 154(b) by 0 days.

(21) Appl. No.: 09/295,400

(22) Filed: Apr. 21, 1999

(30) Foreign Application Priority Data

Nov. 9, 1998 (TW) .................................. 87118595

(51) Int. Cl.$^7$ .................................. G01N 27/26
(52) U.S. Cl. .................. 204/415; 427/2.13; 204/403
(58) Field of Search .................. 204/403, 415; 205/775, 782.5, 792; 427/2.11, 2.13

(56) References Cited

PUBLICATIONS

G. Park et al., "A Rapid Accurate Electrochemical Method for Serum Uric Acid", Analytical Letters, vol. 5, No. 12, pp. 887–896, (1972). Month unknown.

X. Cai et al., "An Improved Voltammetric Method for the Determination of Trace Amounts of Uric Acid with Electrochemically Pretreated Carbon Paste Electrodes", Talanta, vol. 41, No. 3, pp. 407–413, (1994). Month unknown.

A. Yu et al., "Catalytic Oxidation of Uric Acid at the Polyglycine Chemically Modified Electrode and its Trace Determination", Analyst, vol. 122, pp. 839–841, (Aug. 1997).

J. Zen et al., "Square–Wave Voltammetric Determination of Uric Acid by Catalytic Oxidation at a Perfluorosulfonated Ionomer/Ruthenium Oxide Pyrochlore Chemically Modified Electrode", Analytical Chemistry, vol. 67, pp. 1892–1895, (1995). June.

M. Gilmartin et al., "Voltammetric and Amperometric Behavior of Uric Acid at Bare and Surface–Modified Screen–Printed Electrodes: Studies Towards a Disposable Uric Acid Sensor", Analyst, vol. 117, pp. 1299–1303, (1992). Aug.

*Primary Examiner*—T. Tung
*Assistant Examiner*—Alex Noguerola
(74) *Attorney, Agent, or Firm*—Rothwell, Figg, Ernst & Manbeck

(57) ABSTRACT

The present invention relates to a non-enzymatic disposable uric acid detecting electrode strip which directly detects the concentration of uric acid in liquid sample under a low operation voltage of below 400 mV and pH value from 7.0 to 10.0. When the electrode strip is applied to detect the concentration of uric acid in human body, it avoids interference signals caused from any other components in blood and will not be interfered by ascorbic acid unless the concentration of ascorbic acid increases to 15 times of its normal concentration in blood. Not only serum but also whole-blood can be taken as a sample for detecting the uric acid concentration thereof. The uric acid detecting electrode strip is modified by a water soluble redox electron mediator. The electrode strip is easy to carry and can be easily made, particularly mass-produced.

20 Claims, 3 Drawing Sheets

NON-ENZYMATIC DISPOSABLE URIC ACID DETECTING ELECTRODE STRIP, METHOD FOR PRODUCING THE SAME AND ITS USE

BACKGROUND OF THE INVENTION

1. Field of Invention

The present invention relates to a disposable electrode strip which is easy to produce and can detect a concentration of uric acid in a liquid sample, its method for producing the same and its use. More specifically, the present invention relates to a non-enzymatic disposable uric acid electrode strip modified by a water soluble redox electron mediator which accurately detects the concentration of uric acid, avoids any interference caused by other components in the liquid, and is suitable for household use.

2. Description of the Related Art

Uric acid, a final product of the metabolism of purine, is mostly excreted from human body through the kidneys in the form of urine. The concentration of uric acid in blood increases when the source of uric acid increases or the kidney malfunctions. Hyperuricemia is a symptom when the uric acid concentration is above 7 mg/dl. Uric acid is hard to dissolve in blood and will crystallize when supersaturated. The uric acid crystallites deposit on the surface of skin, in joints, and especially in toes and results in gout. The analysis of the uric acid concentration in blood helps to diagnose gout. In addition to gout, hyperuricemia is connected with lymph disturbance, chronic hemolytic anemia, an increase of nucleic acid metabolism and kidney malfunction. High caloric foods and alcohol as well as disturbances of organs and tissues are the main causes of hyperuricemia and even gout. Harm can be prevented and reduced by an early diagnosis and by monitoring. A simple and inexpensive detecting system helps patients to detect the uric acid concentration on their own.

The quantitative analysis of uric acid is basically divided into weight measurement, titration, reduction and enzymatic method. The weight measurement and the titration involve purifying the precipitates of uric acid with magnesium, ammonium or copper and measuring the weight of the precipitates. The weight measurement and the titration are complex but not accurate and therefore they are not suitable in analyzing uric acid. General clinical biochemical analysis so far adopts a reduction or an enzymatic method to detect uric acid. The introduction of reduction and the enzymatic method are in the following paragraphs.

(1) Reduction

The main reaction and theory are as follows:

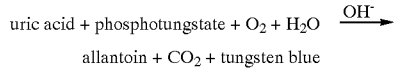

uric acid + phosphotungstate + $O_2$ + $H_2O$ $\xrightarrow{OH^-}$ allantoin + $CO_2$ + tungsten blue The uric acid undergoes an oxidation reaction with phosphotungstate and produces tungsten blue in an alkaline solution with a pH value in the range of 9 to 10. The content of uric acid is measured by spectrophotometer at 660~740 nm. The demerits of the method include: 1) some compounds similar to uric acid and ascorbic acid contained in the blood sample affect the test accuracy; 2) the operation is complex, needs lots of agents which are hard to keep, and should be operated by professionals; 3) the sample must be de-protein pretreated; and 4) the necessary equipment is expensive.

(2) Enzymatic method

The enzymatic method detects uric acid by optical colorimetry and electrochemistry and is classified into uricase-ultravialet absorption, uricase-peroxidase, uricase-catalase and uricase-electrode methods, wherein the former three methods make use of the color of reaction products and quantitatively detect uric acid of products by colorimetry. The automatic bio-analyzers used in central bio-laboratories of hospitals detect uric acid by optical colorimetry. The blood sample should be pretreated to be serum or plasma first. The merits of the automatic bio-analyzers reside in mass detecting, automation and quickness. However, an automatic bio-analyzer cannot be applied in household detecting because it requires professionals to operate, is expensive, and it is particularly hard to store the detecting agents.

The uricase-electrode method detects uric acid by electrochemistry. The electrodes can be divided as enzymatic and non-enzymatic. The former produced by a complex production process is hard to store and thus is only suitable for research. The related prior research of the latter were as follows:

Park G, Adams R N, White W R (Anal. Lett., 1972; 5:887) detected uric acid by measuring current signals produced by an electrochemical oxidation of uric acid on a carbon-based electrode. The reaction system was not accurate because of the interference resulting from ascorbic acid in an acid solution. Several researches tried to avoid the influence of interference and to improve the specificity to uric acid.

For example, X. Cai, K. Kalcher, C. Neuhold and B. Ogorevc (Talanta, 1994; 41:407~413) placed a carbon paste electrode in an alkaline solution and apply 1.4V vs. SCE for 40 seconds to be anodized. This method forced the oxidation potential of uric acid to shift to around 0 mV vs. SCE, increased the response current and distinguishes uric acid from ascorbic acid. The detectable linear ranges were from $3 \times 10^{-8}$ to $2.4 \times 10^{-4}$ M ($5 \times 10^{-4}$ to 4 mg/dl) and the detecting limit was $1.2 \times 10^{-8}$ M ($2 \times 10^{-3}$ mg/dl). The manufacturing process was time-consuming and complex and not suitable for production on a large scale. The electrode could not be easily operated. Most important of all, the linear ranges were out of the normal dianostic range of 2~14 mg/dl.

Ai-min Yu, Hai-li Zhang and Hong-yuan Chen (Analyst, 1997; 122:839~841) modified the surface of glassy carbon electrode by electro-polymerization of polyglycine. The modified electrode could distinguish potential of uric acid (0.45 mV vs. SCE) from ascorbic acid (0.30 mV vs. SCE) and increased the response current of uric acid after redox reaction. The detectable linear ranges were from $5 \times 10^{-8}$ to $4.5 \times 10^{-6}$ M ($8.4 \times 10^{-4}$ to $7.5 \times 10^{-2}$ mg/dl) and the detecting limit was $5 \times 10^{-9}$ M ($8.4 \times 10^{-5}$ mg/dl). The urate sample was prepared by dissolving uric acid in a 0.1M phosphate buffer solution with a pH value of 7.0. The electrode manufacturing process was time-consuming and complex and not suitable for mass production. The electrode costs high, and could not be used as a disposable strip. Besides, the linear ranges were also out of normal diagnostic ranges.

Jyh-Myng Zen and Jen-Sen Tang (Anal. Chem. 1995; 67:1892~1895) modified the glassy carbon electrode by Nafion/$Ru_{2-x}Pb_xO_{7-x}$ (ruthenium oxide pyrochlore) and detected uric acid by Osteryoung square-wave voltammeter. The redox potential of uric acid was +0.65 V vs. Ag/AgCl where the redox potential of ascorbic acid was 0.5 V vs. Ag/AgCl. The electrode would not be interfered with by the ascorbic acid unless the concentration of ascorbic reached to 20 mg/dl level. The electrode worked in the pH value of 1.

The detectable linear ranges were from $7.5 \times 10^{-5}$ to $5 \times 10^{-7}$M ($8.4 \times 10^{-3}$ to 1.26 mg/dl) and the detecting limit was $1.1 \times 10^{-7}$M ($1.8 \times 10^{-3}$ mg/dl). The electrode shared the demerits mentioned above, and also can not be used as a disposable strip.

Markas A. T. Gilmort and John P. Hart (Analyst, 1992; 117:1299~1303) detected uric acid by a screen printing carbon-based electrode modified by Nafion containing L-ascorbic acid oxidase. The modification decreased the interference of ascorbic acid and increased the specificity to uric acid. The optimum reaction condition was at pH value of 5.5 and operation voltage of +0.4 V vs. SCE. The detectable linear ranges were from $5.08 \times 10^{-6}$ to $1.51 \times 10^{-4}$M ($8.5 \times 10^{-2}$ to 2.54 mg/dl) and the detecting limit was $2.54 \times 10^{-4}$M ($4.3 \times 10^{-2}$ mg/dl). The tolerance concentration of ascorbic acid was below 0.53 mM (9.34 mg/dl) so as not to interfere with uric acid. The electrode could be mass-produced but the cost was high and several manufacturing steps are involved. The detectable linear ranges were also not within general diagnostic ranges(2~8 mg/dl). The sample should be pretreated and thus the electrode cannot be operated at home.

SUMMARY OF THE INVENTION

An object of the present invention is to provide a novel and practical non-enzymatic disposable uric acid detecting electrode strip which electrochemically detects uric acid in liquid sample under a low operation voltage of below 400 mV and pH value from 7.0 to 10.0. When being applied in detecting from a blood sample, the strip can directly detect the concentration of uric acid in whole-blood as well as in serum sample and avoid interference signals caused from ascorbic acid.

Another object of the present invention is to provide a novel and practical non-enzymatic uric acid detecting electrode strip modified by a water soluble redox electron mediator which can be screen printed directly. The disposable uric acid detecting electrode strip does not require the use of any expensive uricase and L-ascorbic acid oxidase and can be easily made and mass-produced.

A further object of the present invention is to provide a simplified method for producing disposable non-enzymatic uric acid detecting electrode strip which does not require any bio-active substances and thus simplifies the production method. The method reduces the manufacturing costs and can rapidly proceed on a large scale so that the produced electrode strip is convenient for people to use.

A still further object of the present invention is to provide a method for producing disposable non-enzymatic uric acid detecting electrode strip, wherein the carrier film and the conductive mediator can be produced in one printing step rather than conventional two printing steps for carrier film, conducting film and enzyme.

A still further object of the present invention is to provide a novel, rapid, convenient and safe method for detecting uric acid in a liquid sample. The liquid sample is directly dropped on the disposable non-enzymatic uric acid detecting electrode strip and the uric acid in the sample can be easily detected by a redox reaction. The method is suitable for household use when being applied to detect the human uric acid concentration in the blood.

Other objects of the present invention will be become apparent from the entire disclosure given herein.

DETAILED DESCRIPTION OF THE PREFERRED EMBODIMENTS

The present invention relates to a non-enzymatic and a water soluble redox electron mediator-modified uric acid detecting electrode strip. The detecting electrode strip applied to a detecting system of low operation voltage of below 400 mV can sensitively and specifically detect the concentration of uric acid in liquid by catching signals generated by a redox current of a redox electron mediator and uric acid. The detecting electrode strip would not be interfered with by any other components in liquid. In other words, the non-enzymatic uric acid detecting electrode strip of the present invention, according to the theory of electrochemistry, can directly detect the concentration of uric acid in liquid. When the strip of the present invention is applied to detect the human uric acid concentration, the whole-blood can be taken directly as a sample. Conventional bio-analyzers take serum as a sample only because blood cells in the whole-blood would interfere with the results.

The present invention provides a non-enzymatic disposable uric acid detecting electrode strip which comprises:

an electric insulating substrate;

a conducting film coated on one side of the electric insulating substrate to form isolated and disconnected an anode and a cathode;

an electric insulating film coated on a part of the conducting film, wherein one end of an uncovered anode of the conducting film forms at least a reference electrode and the other end an anode connector, and one end of an uncovered cathode of the conducting film forms at least a working electrode and the other end a cathode connector; and a reaction film comprising a carrier and a conductive mediator and being screen printed on a region containing at least the working electrode and the reference electrode so as to connect the working electrode and the reference electrode individually, wherein the carrier comprises a microcrystalline cellulose, a polymer and a buffer solution; and the conductive mediator comprises an electrolyte with a lower redox potential than that of uric acid.

Figure 1A:
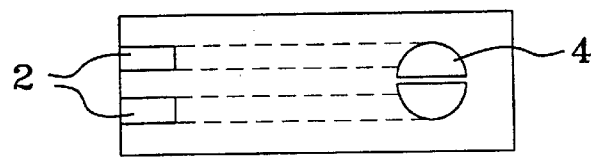
FIG. 1a is a top view diagram of an electrode strip of the present invention.
Figure 1B:
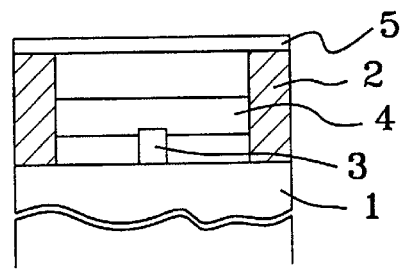
FIG. 1b is a front view diagram of an electrode strip of the present invention.

According to the non-enzymatic disposable uric acid detecting electrode strip of the present invention, FIGS. 1a and 1b are respectively a top view diagram and a front view diagram of an electrode strip of the present invention. The electrode strip structure comprises an electric insulating substrate 1, a conducting film 2 coated on the insulating substrate, an electric insulating film 3 coated on a part of the conducting film 2, and a reaction film 4 for reacting with a sample.

The electric insulating substrate 1 of the present invention has a flat surface as well as an insulation property and is thermal-resistant from 40° C. to 80° C. for thermal processing and increasing the conductivity and adherence of the conducting film 2. The materials suitable for the electric insulating substrate could be any of polyvinyl chloride (PVC), fiber glass (FR-4), polyester suphone, bakelite plate, polyethylene terephthalate (PET) plate, polycarbonate (PC) plate, glass plate and ceramics plate (CEM-1).

The conducting film 2 comprises a set of isolated, disconnected and symmetric anode and cathode so as to connect with a amperometric sensor. The cathode is partially covered by the electric insulating film 3 and two uncovered ends of the cathode are a working electrode and a cathode connector respectively. The working electrode of the cathode is then covered by the reaction film 4 and is used to detect an induced electric effect of samples during the electrochemical reaction of uric acid. The cathode connector is used to connect with a amperometric sensor. The anode is also partially covered by the electric insulating film 3 and two uncovered ends of the anode are a reference electrode and an anode connector respectively. The reference electrode of the anode is covered by the reaction film 4 and cooperates together with the working electrode of the cathode to detect the induced electric effect. The anode connector is also used to connect with the amperometric sensor.

According to the non-enzymatic disposable uric acid detecting electrode strip of the present invention, the electric insulating film 3 is coated on one surface of the electric insulating substrate 1 but does not cover the cathode connector, anode connector, working electrode and reference electrode. The suitable thickness of the electric insulating film 3 is 0.6 mm or above. The region uncovered by the electric insulating film 3 includes the working electrode and the reference electrode and forms a reaction region which is then coated by the reaction film 4 for testing samples.

The reaction film 4, a water soluble redox electron mediator, comprises a carrier and a conductive mediator. The carrier is a slurry material suitable for screen printing and comprises a microcrystalline cellulose, a polymer and a buffer solution. The microcrystalline cellulose is used to absorb a sample because the sample is hydrophilic and hard to attach to a hydrophobic conducting film. The microcrystalline cellulose enhances the absorption of sample and enhances the signals to be transferred to the conducting film. For mass-production, microcrystalline cellulose of the carrier has a size below 100 μm. The microcrystalline cellulose thus can be distributed all over the reaction film area and ensure the signals be thoroughly transferred. The microcrystalline cellulose of the carrier is about 5 to 40% by weight of the reaction film.

The polymer of the carrier is selected from the group consisting of polyvinyl alcohol (PVA), polyvinyl pyrrolidone (PVP), polyethylene glycol (PEG), inkatin, carboxymethyl cellulose (CMC), methyl cellulose and the mixture thereof. The polymer of the carrier is about 5 to 40% by weight of the reaction film. The polymer is to facilitate the reaction film having a certain viscosity for screen printing. The reaction film can therefore be distributed thoroughly.

The buffer solution of the carrier comprises potassium dihydrogen phosphate, dipotassium orthophosphate, salts of boric acid, citric acid or Tris. The buffer solution of the carrier is 1 to 10% by weight of the reaction film. The buffer solution is used to adjust the pH value of from 7.0 to 10.0 for a reaction between the reaction film and uric acid.

The other component of the reaction film is a conductive mediator comprising an electrolyte with a lower redox potential than that of uric acid. The conductive mediator will change from oxidation state to reduction state after reacting with uric acid. The conductive mediator can then reverse to oxidation state by applying a forced voltage. The changes of, such as potential, resistance, or current caused by electrochemical reaction, could be transferred through the conducting film, i.e. from the working electrode and the reference electrode connected with the reaction film to the cathode connector and the anode connector. The uric acid detecting electrode strip, during testing, connects with a amperometric sensor which comprises a voltage output equipment applying a voltage to the electrode strip, a receiver receiving a signal for the potential, resistance, or current changes caused by said electrochemical reaction, and a display equipment transferring the signal to uric acid concentration. One embodiment of the present invention illustrates the use of potassium ferricyanide as a conductive mediator. The conductive mediator of the reaction film is about 2 to 10% by weight of the reaction film.

The present invention can be mainly applied to liquid samples. When taking whole-blood as a sample for detecting uric acid, there will be interference caused by other components, especially ascorbic acid in the blood. To avoid such interference, the present invention controls the uric acid electrode reaction at a low operation voltage of below 400 mV and pH value from 7.0 to 10.0. The ascorbic acid will not interference with uric acid unless its concentration increases to 15 times of its normal concentration in blood. The detecting electrode strip and detecting equipment of the present invention can directly detect the uric acid for household use.

In accordance with the present invention, the reaction film 4 is optionally coated with a protection film 5 to protect the reaction film.

One advantage of the present invention is to eliminate the use of any bio-active substances such as enzymes. Not only does the present invention simplify the production process, but the production cost is reduced, the storage term is increased, and the storage restriction of the detecting electrode strip is released.

Though conventional bio-active detecting electrode strip could be mass produced by screen printing and be disposable, it requires two printing steps. First, the carrier is printed on substrate; then the bio-active substances such as enzyme and a conductive mediator are printed onto the carrier. The enzyme is expensive and requires special storage conditions and equipment. Furthermore, the bio-active substances require strict operation conditions and may scrap products from a whole production line once the operation conditions vary. The non-enzymatic electrode strip of the present invention simplifies the producing process by printing a carrier and a conductive mediator in one step and reduces the production cost.

The present invention further provides a method for producing disposable non-enzymatic uric acid detecting electrode strip which comprises:

(a) coating a conducting film on one side of an electric insulating substrate and forming isolated and disconnected an anode and a cathode;

(b) coating an electric insulating film on a part of the conducting film, wherein one end of an uncovered anode of the conducting film is at least a reference electrode and the other end an anode connector, and one end of an uncovered cathode of the conducting film is at least a working electrode and the other end a cathode connector; and (c) screen printing a reaction film on a region containing at least the working electrode and the reference electrode so as to connect the working electrode and the reference electrode individually, wherein the reaction film comprises a carrier and a conductive mediator, the carrier comprises a microcrystalline cellulose, a polymer and a buffer solution, and the conductive mediator comprises an electrolyte with a lower redox potential than that of uric acid.

Figure 2A:
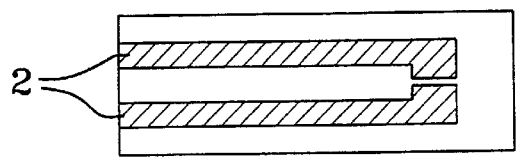
FIG. 2a is a graph showing the production steps of an electrode strip of the present invention involving screen printing on an electric insulating substrate a conducting film containing at least an anode and a cathode.

According to the method for producing disposable non-enzymatic uric acid detecting electrode strip of the present invention, a conducting film 2 is first coated such as by screen printing on one side of a flat substrate 1 to form at least an anode and a cathode which are separately isolated from each other, as shown in FIG. 2a. The material suitable for conducting film could be carbon ink, gold ink, silver ink, the mixture of carbon and silver ink, volatile graphite, copper ink, or the mixture of the above (for example, printing silver ink first and then printing carbon ink). The material is a conductive slurry material suitable for screen printing. After printing, the conducting film is dried at 40 to 80° C.

Figure 2B:
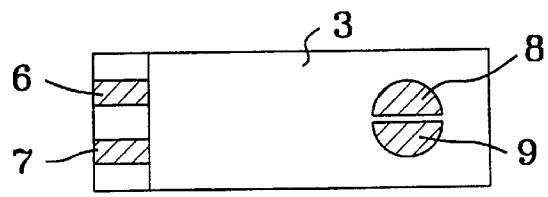
FIG. 2b is a graph showing the production steps of an electrode strip of the present invention involving screen printing an electric insulating film to partially cover on the conducting film (FIG. 2a), wherein the uncovered conducting film forms an anode connector, a cathode connector, a working electrode and a reference electrode.

According to step (b) of the production method of the present invention, an electric insulating film with a thickness of 0.6 mm or above is partially printed onto the conducting film. The uncovered parts of the conducting film form a cathode connector 6, an anode connector 7, a working electrode 8 and a reference electrode 9, as shown in FIG. 2b. An area formed by the working electrode 8 and the reference electrode 9 in a circle or any other suitable shape is an area of reaction film.

Figure 2C:
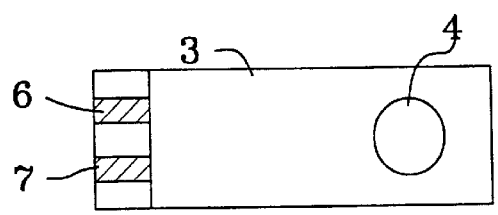
FIG. 2c is a graph showing the production steps of an electrode strip of the present invention involving screen printing a carrier and a conductive mediator on a reaction film region formed by the working electrode and the reference electrode.

In step (c), conductive slurry materials containing microcrystalline cellulose, a polymer (for example: polyvinyl alcohol, polyvinyl pyrrolidone, polyethylene glycol, inkatin, carboxymethyl cellulose, methyl cellulose or the mixture of the above), a buffer solution (for example: potassium dihydrogen phosphate, dipotassium orthophosphate, salts of boric acid, citric acid or Tris) and a conductive mediator are screen printing on the circle area of the reaction film 4, as shown in FIG. 2c.

Figure 2D:
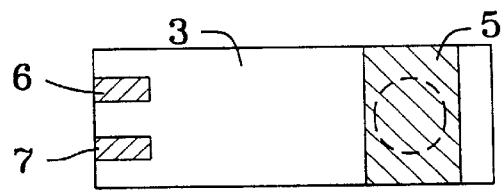
FIG. 2d is a graph showing the production steps of an electrode strip of the present invention involving coating a protection film on the reaction film.

According to the production method of the present invention, the reaction film can be further dried at 40 to 80° C. A protection film 5 is optionally coated on and around the circle area of the reaction film 4, as shown in FIG. 2d. The disposable non-enzymatic uric acid detecting electrode strip is therefore produced.

Several conventional screen printing technologies can be used in the method for producing disposable non-enzymatic uric acid detecting electrode strip of the present invention. Moreover, a new screen printing technology disclosed by one of the inventors of the present invention and contained in R.O.C. patent application number 85,109,554 could also be applied in the production method of the present invention.

The detecting method of non-enzymatic electrode strip of the present invention can proceed easily by using electrochemical detecting equipment. The reaction current caused by the redox reaction of uric acid can be detected in a uric acid detecting equipment by dropping a whole-blood sample on the reaction area of the non-enzymatic disposable uric acid detecting electrode strip of the present invention. Such an electrochemical reaction technology is commonly applied in electrochemical blood sugar monitor for detecting blood sugar. The method of directly detecting uric acid in whole-blood is novel and first disclosed in the present invention by using a redox electron mediator to transfer signals of the redox reaction of uric acid and by controlling the reaction at pH value from 7.0 to 10.0 as well as a low operation voltage of below 400 mV to avoid the interference result from glucose and ascorbic acid in blood.

The present invention also provides an uric acid detecting equipment comprises a disposable non-enzymatic uric acid detecting electrode strip and a amperometric sensor directly analyzing uric acid in liquid sample (including blood), wherein the electrode strip comprises:

an electric insulating substrate;

a conducting film coated on one side of the substrate to form isolated and disconnected an anode and a cathode;

an electric insulating film coated on a part of the conducting film, wherein one end of an uncovered anode of the conducting film forms at least a reference electrode and the other end an anode connector, and one end of an uncovered cathode of the conducting film forms at least a working electrode and the other end a cathode connector; and a reaction film comprising a carrier and a conductive mediator and being screen printed on a region containing at least the working electrode and the reference electrode so as to connect the working electrode and the reference electrode individually, wherein the carrier comprises a microcrystalline cellulose, a polymer and a buffer solution; and the conductive mediator comprises an electrolyte with a lower redox potential than that of uric acid.; and the amperometric sensor is connected to the anode connector and the cathode connector of the uric acid detecting electrode strip and comprises a voltage output equipment, a signal receiver and a display equipment; in which the voltage output equipment provides a voltage of below 400 mV to the reaction film of the uric acid detecting electrode strip so as to oxidize the conductive mediator from reduction state to oxidation state after being reacted with uric acid of the sample; the signal receiver receives a current, voltage or resistance change generated during a redox reaction and transmits the change to the display equipment to display the concentration of uric acid in the sample.

The detecting conditions at low operation voltage of below 400 mV and pH value from 7.0 to 10.0 of the present invention avoid interference caused by other oxidizing components. The Vitamin C will not interfere with uric acid unless its concentration is 15 times of its normal concentration as found in human body. Though the redox potential of Vitamin C is lower than that of uric acid, Vitamin C causes less signal under the operation conditions of the present invention. The present invention does not require any expensive uricase and can precisely detect the uric acid concentration.

The following examples are exemplified to describe in detail the present invention but not to confine the present invention.

EXAMPLE 1

On one flat side of polyvinyl chlorine (PVC) substrate, carbon ink was screen printed to form a conducting film 2 comprising a set of isolated and disconnected anode and cathode and then dried at 40 to 80° C. An electric insulating film 3 with a thickness of about 0.6 mm was subsequently screen printed on the conducting film 2 partially. The uncovered part of the conducting film formed a cathode connector 6, a anode connector 7, a working electrode 8 and a reference electrode 9. The circle area formed by working electrode 8 and reference electrode 9 was an area of reaction film 4.

Slurry materials comprising the following components and proportions were then screen printing on the circle area of reaction film 4.

| | |
|---|---|
| Microcrystalline cellulose (diameter: average about 20 μm) | 21.2% |
| PEG, polyethylene glycol | 0.3% |
| PVP, polyvinyl pyrrolidone | 13.4% |
| $K_2HPO_4$ | 0.04% |
| $KH_2PO_4$ | 0.1% |
| $H_2O$ | 59.96% |
| Potassium ferricyanide | 5% |

After screen printing the reaction film 4, it was dried at 40 to 80° C. A protection film 5 was coated on and around the circle area of reaction film 4. The disposable non-enzymatic uric acid detecting electrode strip was produced through the production steps of the above.

Figure 3:
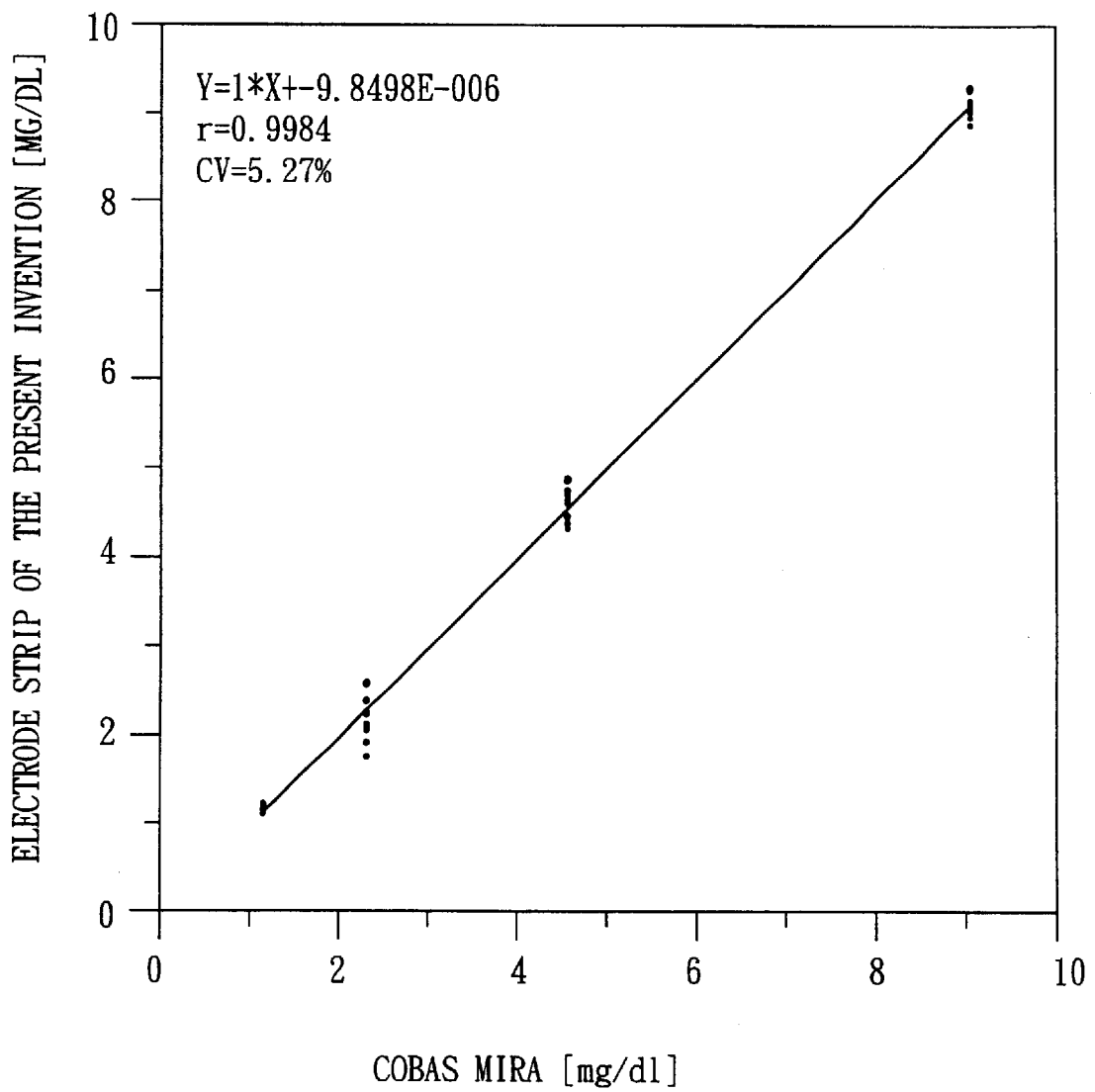
FIG. 3 is a graph showing comparative results of the concentration of uric acid in serum detected by COBAS MIRA bio-analyzer and by the electrode strip of the present invention.
Figure 4:
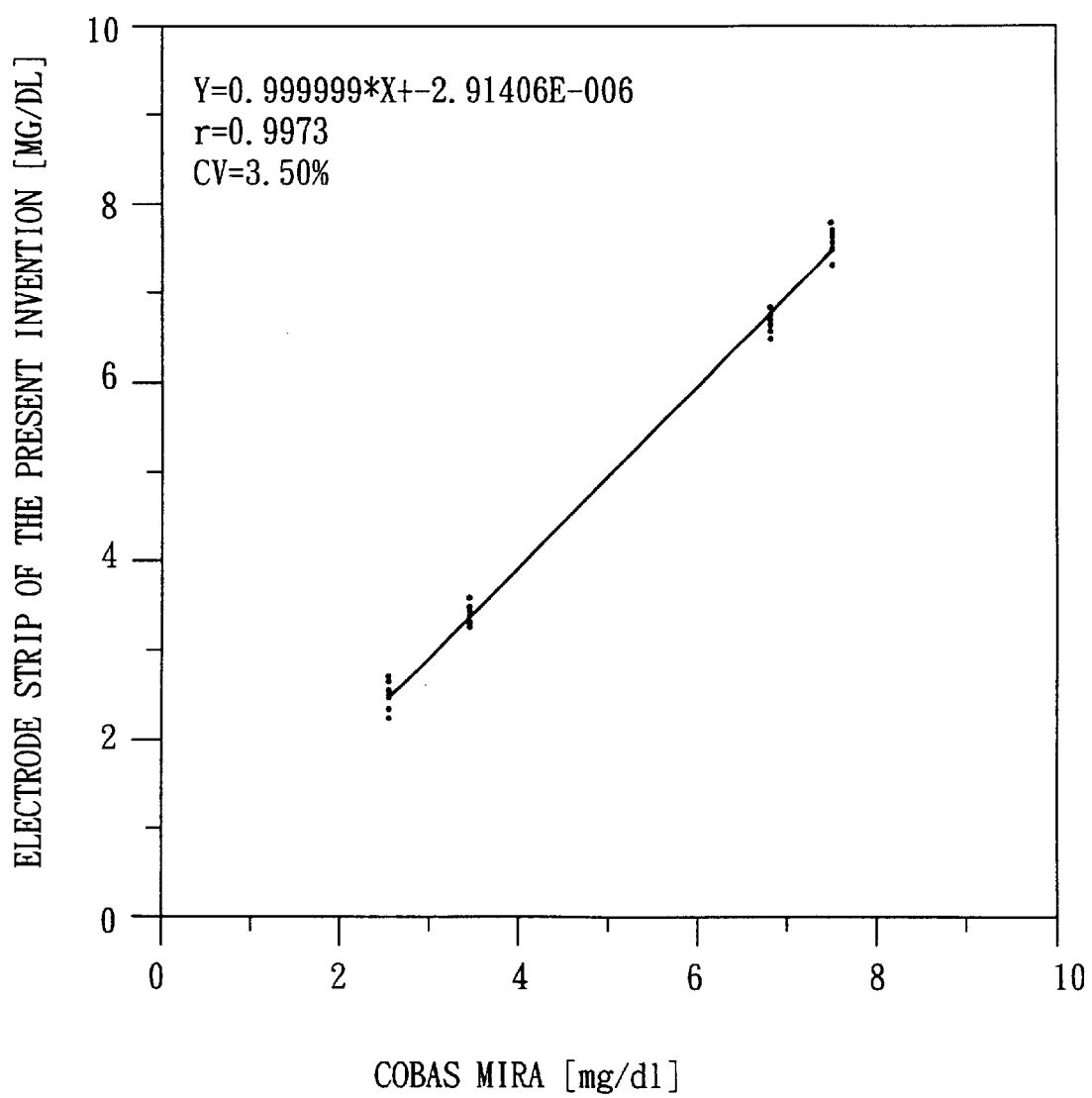
FIG. 4 is a graph showing comparative results of the concentration of uric acid in serum detected by COBAS MIRA bio-analyzer and of the concentration of uric acid in whole-blood of the same sample detected by the electrode strip of the present invention.

The uric acid in blood can be detected by the above obtained disposable non-enzymatic uric acid detecting electrode strip of the present invention by taking whole-blood as a sample. The test results were the same as the uric acid concentration detected by any conventional method. FIG. 3 shows the comparative results of the uric acid concentration in serum by COBAS MIRA bio-analyzer and the detecting electrode strip of the present invention; and FIG. 4 shows the comparative results of the uric acid concentration in serum by COBAS MIRA bio-analyzer and the uric acid concentration in whole-blood of the same sample by the detecting electrode strip of the present invention.

The results show that the disposable non-enzymatic uric acid detecting electrode strip of the present invention can precisely detect the uric acid concentration in blood by taking whole-blood as a sample and does not require any pretreatment.

EXAMPLE 2

The steps of example 1 were repeated, except that the components and proportions of slurry materials were changed as follows:

| | |
|---|---|
| Microcrystalline cellulose (diameter: average about 20 μm) | 21.2% |
| PEG, polyethylene glycol | 19.8% |
| $K_2HPO_4$ | 0.7% |
| Citric acid | 1.5% |
| $H_2O$ | 52.8% |
| Potassium ferricyanide | 4% |

The uric acid in blood can be detected by the above obtained disposable non-enzymatic uric acid detecting electrode strip of the present invention by taking whole-blood as a sample. The test results were the same as the uric acid concentration detected by any conventional method. The results show that the disposable non-enzymatic uric acid detecting electrode strip of the present invention can precisely detect the uric acid concentration in blood by taking whole-blood as a sample and does not require any pretreatment.

EXAMPLE 3

The steps of example 1 were repeated, except that the components and proportions of slurry materials were changed as follows:

| | |
|---|---|
| Microcrystalline cellulose (diameter: average about 20 μm) | 35% |
| PVA, polyvinyl alcohol | 13% |
| PVP, polyvinyl pyrrolidone | 7% |
| $K_2HPO_4$ | 0.7% |
| $H_2O$ | 36.8% |
| Potassium ferricyanide | 6% |

The uric acid in blood can be detected by the above obtained disposable non-enzymatic uric acid detecting electrode strip of the present invention by taking whole-blood as a sample. The test results were the same as the uric acid concentration detected by any conventional method. The results show that the disposable non-enzymatic uric acid detecting electrode strip of the present invention can precisely detect the uric acid concentration in blood by taking whole-blood as a sample and does not require any pretreatment.

EXAMPLE 4

The steps of example 1 were repeated, except that the components and proportions of slurry materials were changed as follows:

| | |
|---|---|
| Microcrystalline cellulose (diameter: average about 20 μm) | 20% |
| PVP, polyvinyl pyrrolidone | 2.8% |
| PVA, polyvinyl alcohol | 3.5% |
| PEG, polyethylene glycol | 12% |
| inkatin | 2.1% |
| $K_2HPO_4$ | 0.7% |
| Citric acid | 1.5% |
| $H_2O$ | 54.4% |
| Potassium ferricyanide | 3% |

The uric acid in blood can be detected by the above obtained disposable non-enzymatic uric acid detecting electrode strip of the present invention by taking whole-blood as a sample. The test results were the same as the uric acid concentration detected by any conventional method. The results show that the disposable non-enzymatic uric acid detecting electrode strip of the present invention can precisely detect the uric acid concentration in blood by taking whole-blood as a sample and does not require any pretreatment.

From the examples mentioned hereinabove, it is clear that the uric acid detecting electrode strip of the present invention does not require any bio-active substances and thus the production steps are simplified and shortened. Furthermore, the present invention can take whole-blood as a testing sample and precisely detect the uric acid concentration at a low operation voltage of below 400 mV and pH value from 7.0 to 10.0.

With the disclosed invention, apparently numerous modifications and variations can be made without departing from the scope and spirit of this the present invention. Therefore the present invention is intended to be limited only as indicated in the following claims.

What is claimed is:

1. A non-enzymatic disposable uric acid detecting electrode strip which comprises:
   an electric insulating substrate;
   a conducting film coated on one side of the substrate to form isolated and disconnected an anode and a cathode;
   an electric insulating film coated on a part of the conducting film, wherein one end of an uncovered anode of the conducting film forms at least a reference electrode and the other end an anode connector, and one end of an uncovered cathode of the conducting film forms at least a working electrode and the other end a cathode connector; and
   a reaction film comprising a carrier and a conductive mediator and being screen printed on a region containing at least the working electrode and the reference electrode so as to connect the working electrode and the reference electrode individually, wherein the carrier comprises a microcrystalline cellulose, a polymer and a buffer solution; and the conductive mediator comprises an electrolyte with a lower redox potential than that of uric acid; wherein said reaction film does not contain an enzyme.

2. The uric acid detecting electrode strip in claim 1, in which the reaction film is used to contact a sample and reacts electrochemically.

3. The uric acid detecting electrode strip of claim 1, in which the carrier is a slurry material suitable for screen printing.

4. The uric acid detecting electrode strip of claim 1, in which the microcrystalline cellulose of the carrier has a size below 100 $\mu$m.

5. The uric acid detecting electrode strip of claim 1, in which the microcrystalline cellulose of the carrier is about 5 to 40% by weight of the reaction film.

6. The uric acid detecting electrode strip of claim 1, in which the polymer of the carrier is selected from the group consisting of polyvinyl alcohol (PVA), polyvinyl pyrrolidone (PVP), polyethylene glycol (PEG), inkatin, carboxymethyl cellulose (CMC), methyl cellulose and the mixture thereof.

7. The uric acid detecting electrode strip of claim 1, in which the polymer of the carrier is about 5 to 40% by weight of the reaction film.

8. The uric acid detecting electrode strip of claim 1, in which the buffer solution of the carrier comprises potassium dihydrogen phosphate, dipotassium orthophosphate, salts of boric acid, citric acid or Tris.

9. The uric acid detecting electrode strip of claim 1, in which the buffer solution of the carrier is 1 to 10% by weight of the reaction film.

10. The uric acid detecting electrode strip of claim 1, in which the buffer solution of the carrier has a pH value of from 7.0 to 10.0

11. The uric acid detecting electrode strip of claim 1, in which the conductive mediator is potassium ferricyanide.

12. The uric acid detecting electrode strip of claim 1, in which the conductive mediator of the reaction film is about 2 to 10% by weight of the reaction film.

13. The uric acid detecting electrode strip of claim 1 being dried at a temperature in the range from 40° C. to 80° C.

14. The uric acid detecting electrode strip of claim 1, in which the reaction film is further covered with a protection film.

15. A method for producing disposable non-enzymatic uric acid detecting electrode strip which comprises:
   (a) coating a conducting film on one side of an electric insulating substrate and forming isolated and disconnected an anode and a cathode;
   (b) coating an electrode insulating film on a part of the conducting film, wherein one end of an uncovered anode of the conducting film is at least a reference electrode and the other end an anode connector, and one end of an uncovered cathode of the conducting film is at least a working electrode and other end a cathode connector; and
   (c) screen printing a reaction film on a region containing at least the working electrode and the reference electrode so as to connect the working electrode and the reference electrode individually, wherein the reaction film comprises a carrier and a conductive mediator, the carrier comprises a microcrystalline cellulose, a polymer and a buffer solution, and the conductive mediator comprises an electrolyte with a lower redox potential than that of uric acid; whereby said reaction film does not contain an enzyme.

16. The method of claim 15, in which the electric insulating film has a thickness of 0.6 mm or above.

17. An uric acid detecting equipment comprises a disposable non-enzymatic uric acid detecting electrode strip and an amperometric sensor directly analyzing uric acid in a liquid sample,
   wherein the electrode strip comprises:
      an electrode insulating substrate;
      a conducting film coated on one side of the substrate to form isolated and disconnected an anode and a cathode;
      an electrode insulating film coated on a part of the conducting film, wherein one end of an uncovered anode of the conducting film forms at least a reference electrode and the other end an anode connector, and one end of an uncovered cathode of the conducting film forms at least a working electrode and the other end a cathode connector; and
      a reaction film comprising a carrier and a conductive mediator and being screen printed on a region containing at least the working electrode and the reference electrode so as to connect the working electrode and the reference electrode individually, wherein the carrier comprises a microcrystalline cellulose, a polymer and a buffer solution; and the conductive mediator comprises an electrolyte with a lower redox potential than that of uric acid, and wherein said reaction film does not contain an enzyme;
   the amperometric sensor is connected to the anode connector and the cathode connector of the uric acid detecting electrode strip and comprises a voltage output equipment, a signal receiver and a display equipment; in which the voltage output equipment provides a voltage of below 400 mV to the reaction film of the uric acid detecting electrode strip so as to oxidize the conductive mediator from reduction state to oxidation state after being reacted with uric acid of the sample; the signal receiver receives a current, voltage or resistance change generated during a redox reaction and transmits the change to the display equipment to display the concentration of uric acid in the sample.

18. The uric acid detecting equipment of claim 17, in which the uric acid detecting electrode strip is disposable.

19. The uric acid detecting equipment of claim 17, in which the liquid sample is blood.

20. The uric acid detecting equipment of claim 17, wherein the amperometric sensor is controlled to operate at a low operation voltage of below 400 mV and a pH value in the range from 7.0–10.0.

* * * * *